United States Patent
Dias et al.

(10) Patent No.: US 10,376,470 B2
(45) Date of Patent: *Aug. 13, 2019

(54) ORAL TABLET FORMULATION CONSISTING OF FIXED COMBINATION OF ROSUVASTATIN AND EZETIMIBE FOR TREATMENT OF HYPERLIPIDEMIA AND CARDIOVASCULAR DISEASES

(71) Applicant: Althera Life Sciences, LLC, Morristown, NJ (US)

(72) Inventors: Marie Charmaine Dias, Morristown, NJ (US); Chandir Ramani, Brapton (CA)

(73) Assignee: Althera Life Sciences, LLC, Morristown, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/687,492

(22) Filed: Aug. 27, 2017

(65) Prior Publication Data

US 2017/0354604 A1    Dec. 14, 2017

Related U.S. Application Data

(63) Continuation-in-part of application No. 14/350,905, filed as application No. PCT/US2013/039018 on May 1, 2013, now Pat. No. 9,763,885.

(60) Provisional application No. 61/641,013, filed on May 1, 2012.

(51) Int. Cl.
| | |
|---|---|
| *A61K 9/00* | (2006.01) |
| *A61K 31/00* | (2006.01) |
| *A61K 9/24* | (2006.01) |
| *A61K 31/505* | (2006.01) |
| *A61K 31/397* | (2006.01) |
| *A61K 9/20* | (2006.01) |
| *A61K 9/28* | (2006.01) |

(52) U.S. Cl.
CPC ........... *A61K 9/209* (2013.01); *A61K 9/0053* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2095* (2013.01); *A61K 9/2893* (2013.01); *A61K 31/397* (2013.01); *A61K 31/505* (2013.01)

(58) Field of Classification Search
CPC .............. A61K 2300/00; A61K 31/397; A61K 31/505; A61K 9/209; A61K 9/0053; A61K 9/2009; A61K 9/2013; A61K 9/2018; A61K 9/2027; A61K 9/2054; A61K 9/2059; A61K 9/2095; A61K 9/2893; A61K 9/2086
See application file for complete search history.

(56) References Cited

U.S. PATENT DOCUMENTS

| | | | | |
|---|---|---|---|---|
| 2007/0087050 A1* | 4/2007 | Jansen | ................. | A61K 9/0056 424/464 |
| 2008/0033030 A1* | 2/2008 | Capua | ................. | A61K 9/2027 514/419 |
| 2010/0204195 A1* | 8/2010 | Lulla | ..................... | A61K 9/209 514/210.02 |
| 2010/0247645 A1* | 9/2010 | Curdy | ................. | A61K 31/165 424/468 |
| 2011/0262497 A1 | 10/2011 | Injac et al. | | |
| 2013/0310420 A1* | 11/2013 | Hsiao | .................... | A61K 47/02 514/311 |
| 2015/0164809 A1* | 6/2015 | Nishida | ................. | A61K 31/47 514/311 |

FOREIGN PATENT DOCUMENTS

| | | | | |
|---|---|---|---|---|
| EP | 2233133 A1 * | 9/2010 | ........... | A61K 9/2853 |
| WO | WO-2009024889 A2 * | 2/2009 | ........... | A61K 31/366 |
| WO | 2010021608 A1 | 2/2010 | | |
| WO | 2011019326 A2 | 2/2011 | | |
| WO | 2011139256 A2 | 11/2011 | | |
| WO | 2012064307 A1 | 5/2012 | | |

OTHER PUBLICATIONS

European Patent Office, Communication pursuant to Article 94(3) EPC, dated Apr. 6, 2018 in EP patent application No. 13785009.5.

* cited by examiner

*Primary Examiner* — Robert A Wax
*Assistant Examiner* — Olga V Tcherkasskaya
(74) *Attorney, Agent, or Firm* — Berggren LLP

(57) ABSTRACT

Solid dosage formulations containing a combination of rosuvastatin and ezetimibe, as well as methods of making such solid dosage forms and method of treating patients with fixed combination solid dosage forms of rosuvastatin and ezetimibe are provided here.

7 Claims, 1 Drawing Sheet

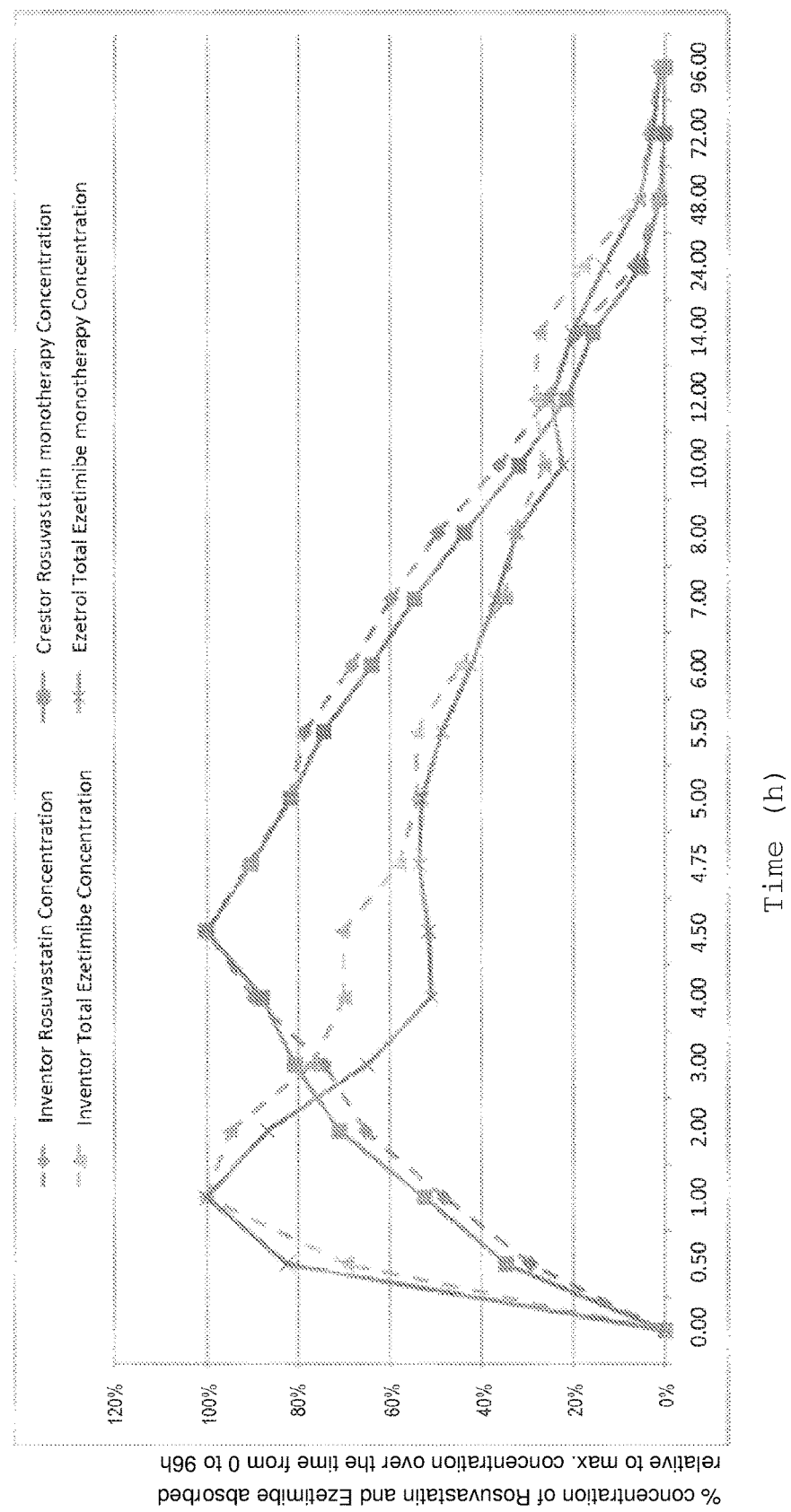

ORAL TABLET FORMULATION CONSISTING OF FIXED COMBINATION OF ROSUVASTATIN AND EZETIMIBE FOR TREATMENT OF HYPERLIPIDEMIA AND CARDIOVASCULAR DISEASES

RELATED APPLICATION

This application is a continuation in part application of U.S. patent application Ser. No. 14/350,905, filed on Apr. 28, 2014 which claims the benefit of U.S. Provisional Application Ser. No. 61/641,013, filed on May 1, 2012. The entire teachings of the above applications are incorporated herein by reference.

BACKGROUND OF THE INVENTION

1. Field of Invention

The present invention is directed to solid dosage formulations containing a combination of rosuvastatin and ezetimibe, as well as to methods of making such solid dosage forms and method of treating patients with fixed combination solid dosage forms of rosuvastatin and ezetimibe.

2. Related Background Art

Cardiovascular disease is one of the largest causes of death in the US, Europe, and also developing nations such as Brazil, Mexico, Russia, China, Turkey and India. Throughout the WHO (World Health Organization) European Region, cardiovascular disease is estimated to account for more than 5 million deaths as well as almost one-quarter of the region's disease burden; WHO estimates 8.7% of the total disease burden in Europe is due to high blood cholesterol, and presence of high levels of Low Density lipids (LDL). Rosuvastatin is an inhibitor of 3-hydroxy-3-methyl-glutaryl coenzyme A (HMG CoA reductase inhibitor) that works by inhibiting the enzyme HMG CoA reductase; HMG CoA is one of the key regulators of cholesterol synthesis in the liver and blockade of the enzyme leads to substantial reduction in total cholesterol (TC), low density lipoprotein cholesterol (LDL-C) and very low-density lipoprotein cholesterol (VLDL-C). Ezetimibe is a compound that also reduces TC and LDL-C but by a different mechanism as it binds cholesterol in the intestine, thereby reducing intestinal absorption of cholesterol. The rosuvastatin and ezetimibe molecules may be selected from any of those disclosed in U.S. Pat. Nos. RE 37,721; 5,260,440; 5,688,990; 5,656,624; 5,624,920; 5,698,548; 5,627,176; 5,633,246; 5,688,785; 5,688,787; 5,744,467; 5,756,470; 5,767,115.

It has been seen in clinical studies that the patients treated with both rosuvastatin and ezetimibe achieve higher levels of LDL reduction compared to individual therapy of rosuvastatin or ezetimibe alone. Hence there is significant value in a fixed combination of rosuvastatin and ezetimibe if such a formulation can be shown having the same Area Under Curve (AUC) as each of the two components taken together, which is demonstrated in bioequivalence (BE) studies. As used herein, "fixed-combination" refers to a combination of two drugs or active ingredients presented in a single dosage unit such as tablet or a capsule; further as used herein, "free-combination" refers to a combination of two drugs or active ingredients dosed simultaneously but as two dosage units. Such a fixed combination in comparison to individual consumption of the two active ingredients will improve ease of administration, create convenience for the patients that need both the individual drugs and improve compliance in patients who cannot be controlled on either product alone. This formulation, when used will increase the compliance in reduction of LDL and thereby reduce the cardiovascular risk of patients consuming this formulation compared to the monotherapy consumption of either rosuvastatin or ezetimibe alone.

Accordingly, a fixed combination solid dosage formulation of rosuvastatin and ezetimibe that is bioequivalent to corresponding free-combination would be desirable.

SUMMARY OF THE INVENTION

In a first aspect, the present invention is an orally consumed fixed combination formulation of both rosuvastatin and ezetimibe in one tablet that is expected to have the same Area Under Curve as two active ingredients taken together individually orally, and pharmaceutically acceptable additives suitable for the preparation. In preferred embodiments of this invention, the rosuvastatin is in the form of rosuvastatin calcium and the pharmaceutically acceptable additives are selected from diluents, disintegrants, glidants, lubricants, colorants and combinations thereof.

In the preferred embodiments of this invention, the solid dosage form is a bi-layer tablet. The amount of rosuvastatin employed in such bi-layer tablets preferably ranges from 2.5 mg, preferably 5 mg, to 40 mg, including 5 mg, 10 mg and 20 mg. The amount of ezetimibe ranges from 5 mg to 20 mg, preferably 10 mg.

In a second aspect, the present invention leads to creation of a novel formulation that overcomes significant problems encountered during the formulation of combining rosuvastatin and ezetimibe in an oral solid dosage form due to inherent characteristics of rosuvastatin and ezetimibe enumerated as follows: (a) Rosuvastatin calcium is prone to oxidative and moisture mediated degradation both leading to formation of a lactone impurity. This reaction can be arrested in presence of basic milieu; (b) Ezetimibe is practically insoluble in water. While cellulose is the normal excipient that would be used for formulations with rosuvastatin, there is a significant interaction of microcrystalline cellulose with ezetimibe, which makes use of such excipient difficult. Microcrystalline cellulose was found to bind with ezetimibe thereby retarding the drug release from the formulation, which would make it not bioequivalent to individually consumed ezetimibe. (c) While rosuvastatin is more stable in near neutral to alkaline pH, the same is detrimental to ezetimibe. Hence it is important to separate the two individual molecules, which creates a significant product development challenge, (d) Solubility issues of ezetimibe raise the challenge of creating a formulation that achieves the right level of in-vitro dissolution as well as is bioequivalent in a combination form to the individual ezetimibe consumption.

Considering the above challenges, the invention describes a novel approach which separates the two active ingredients—rosuvastatin and ezetimibe in two almost completely separate parts, uses microcrystalline cellulose for the formulation of rosuvastatin, but keeps it separate from ezetimibe and follows a unique process of dissolving ezetimibe and mounting it on lactose, or mannitol to enhance the solubility of ezetimibe when used in combination with rosuvastatin to create a formulation that is bioequivalent and has similar Cmax and area under curve as two individual tablets of rosuvastatin and ezetimibe consumed together. This approach then creates a bi-layer tablet, which has one solid layer of ezetimibe composition and a solid layer of rosuvastatin. This formulation then overcomes the above significant development challenges and enables a fixed combination formulation that has simultaneously: a) similar dissolution profile to individual active ingredients, and bioequivalence of the two individual active ingredients compared to consumption of two separate tablets of rosuvastatin and ezetimibe, b) a stable formulation despite the incompatibilities of two component molecules—rosuvastatin and ezetimibe, and c) enables the benefit of reducing the cholesterol levels in patients and reducing the cardiovascular risk in patients compared to monotherapies.

In a third aspect, the present invention is directed to a method of making a solid dosage bi-layer form of rosuvastatin and ezetimibe comprising the steps of: (a) blending rosuvastatin calcium with pre-gelatinized starch, calcium hydrogen phosphate, microcrystalline cellulose and crospovidone, passing through sieve and lubricating the blend with lubricant such as sodium stearyl fumarate to create the rosuvastatin layer blend, (b) mixing ezetimibe with a wetting agent such as sodium lauryl sulphate, and disperse material in sufficient quantity of isopropyl alcohol and dichloromethane mixture, (c) absorbing the dispersion on lactose or mannitol, and mix thoroughly, (d) air drying the dispersion, passing through sieve, mix with croscarmellose sodium, and blend, (e) granulating the mix with polyvinylpyrrolidone solution and dry to obtain the ezetimibe granules, (f) creating the desired bi-layer tablet by compressing the two distinctly different sets of granules as desired in the second aspect of the invention in a bi-layer compression machine, followed by film coating the oral dosage form.

In a fourth aspect, this invention is directed to solid dosage forms of rosuvastatin and ezetimibe made according to the method of the third aspect.

A fifth aspect of this invention is directed to a method of treating hyperlipidemia, cardiovascular diseases, congestive heart failure, myocardial infarction, atherosclerosis comprising administering a solid dosage form of rosuvastatin and ezetimibe in combination to a patient in need of such a treatment. In a preferred embodiment, the solid dosage form is orally administered to the subject.

DESCRIPTION OF THE FIGURE

FIG. 1. Average Release pattern of Concentration of Rosuvastatin and Ezetimibe when administered to forty (40) healthy human volunteers, X-Axis depicts time, and Y-axis depicts % concentration of rosuvastatin or ezetimibe absorbed relative to maximum concentration over varying time points from 0 to 96 hours.

DETAILED DESCRIPTION OF THE INVENTION

The present invention relates to solid dosage formulations containing a combination of rosuvastatin and ezetimibe, as well as to methods of making such solid dosage forms and method of treating patients with fixed combination solid dosage forms of rosuvastatin and ezetimibe.

The first embodiment of the invention is a fixed combination orally consumed formulation of both rosuvastatin and ezetimibe in one tablet that is expected to have same Area Under Curve as two active ingredients taken together individually orally, and pharmaceutically acceptable additives suitable for the preparation. In preferred embodiments of this invention, the rosuvastatin is in the form of rosuvastatin calcium and the pharmaceutically acceptable additives are selected from the diluents, disintegrants, glidants, lubricants, colorants and combinations thereof. The preferred solid dosage form is a bi-layer tablet.

Rosuvastatin and ezetimibe suitable for use in the present invention can be purchased from commercial sources or can be prepared according to known methods. Any form of rosuvastatin or ezetimibe may be used for this invention.

The amount of rosuvastatin employed in such bi-layer tablets preferably ranges from 2.5 mg, preferably 10 mg, to 40 mg, including 5 mg, 10 mg and 20 mg. The amount of ezetimibe ranges from 5 mg to 20 mg, and is preferably 10 mg.

In a second embodiment, the present invention leads to a novel formulation that overcomes significant problems encountered during the formulation of combining rosuvastatin and ezetimibe in an oral solid dosage form due to inherent characteristics of rosuvastatin and ezetimibe enumerated as follows: (a) Rosuvastatin calcium is prone to oxidative and moisture mediated degradation both leading to formation of a lactone impurity. This reaction can be arrested in presence of basic millieu, (b) Ezetimibe is practically insoluble in water. While cellulose is the normal excipient that would be used for formulations with rosuvastatin, there is a significant interaction of microcrystalline cellulose with ezetimibe, which makes use of such excipient difficult. Microcrystalline cellulose was found to bind with ezetimibe thereby retarding the drug release from the formulation, which would make it not bioequivalent to individually consumed ezetimibe. (c) While rosuvastatin is more stable in near neutral to alkaline pH, the same is detrimental to ezetimibe. Hence it is important to separate the two individual molecules, which creates a significant product development challenge, (d) Solubility issues of ezetimibe raise the challenge of creating a formulation that achieves the right level of in-vitro dissolution as well as is bioequivalent in a combination form to the individual ezetimibe consumption.

The above challenges were proven by a number of dissolution tests conducted on the formulation described in Table 1, which demonstrates the challenge in creating a formulation that is similar to the individually consumed tablets.

TABLE 1

COMPARATIVE DISSOLUTION PROFILE OF EZETIMIBE IN ROSUVASTATIN 20 mg & EZETIMIBE 10 mg TABLETS

| Appearance of the tablet # | White colored round shaped tablets Basket at 75 RPM |
|---|---|
| Time in min | No of tablets 6 tablets |
| 5 | 45 |
| 10 | 81 |
| 20 | 87 |
| 30 | 89 |
| 45 | 91 |

Considering above challenges, the invention describes a novel approach which separates the two active ingredients—rosuvastatin and ezetimibe in two almost completely separate parts or layers, uses microcrystalline cellulose for the formulation of rosuvastatin, but keeps it separate from ezetimibe and follows a unique process of dissolving ezetimibe and mounting it on lactose or on mannitol to enhance the solubility of ezetimibe when used in combination with rosuvastatin to create a formulation that is bioequivalent and has similar Cmax and area under curve as two individual tablets of rosuvastatin and ezetimibe consumed together. This approach then creates a bi-layer tablet, which has one solid layer of ezetimibe composition and a solid layer of rosuvastatin. This formulation then overcomes the above significant development challenges and enables creating a fixed combination formulation that has simultaneously: a) similar dissolution profile to individual active ingredients, and bioequivalence of the two individual active ingredients compared to consumption of two separate tablets of rosuvastatin and ezetimibe, b) a stable formulation despite the incompatibilities of two component molecules—rosuvastatin and ezetimibe, and c) enables the benefit of reducing the cholesterol levels in patients and reducing the cardiovascular risk in patients compared to monotherapies.

In this embodiment, the formulation with the rosuvastatin layer, that is the top layer that consists of rosuvastatin as the active ingredient, with excipients such as starch 1-15% of the weight of the rosuvastatin layer, dicalcium phosphate 0.5-10% of the weight of the rosuvastatin layer, microcrystalline cellulose 20-90% of the weight of the rosuvastatin layer, crospovidone 2-30% of the weight of the rosuvastatin layer, and lubricants such as sodium stearyl fumarate 0.1-2% of the weight of the rosuvastatin layer. In addition the layer may contain an antioxidant such as butylated hydroxyl anisole 0.05 to 2% of the weight of rosuvastatin layer and a dispersion agent such as Aerosil 1-10% of the rosuvastatin layer. This formulation in a separate layer of rosuvastatin enables a good dissolution of rosuvastatin at the same time avoids the oxidative effects leading to degeneration into lactone, thereby making the rosuvastatin layer more stable while placing the layer on top of the ezetimibe layer.

In this aspect, the formulation with the ezetimibe layer, that is the bottom layer consists of ezetimibe as the active ingredient, with excipients as a surfactant such as sodium lauryl sulphate 2-20% of the ezetimibe layer, lactose or mannitol 20-90% of the ezetimibe layer, a disintegrant such as croscarmellose 5-30% of the ezetimibe layer, a binder such as polyvinylpyrrolidone 0.5-10% of the ezetimibe layer, and magnesium stearate 0.2-5% of the ezetimibe layer.

Method

In a third embodiment, the present invention is directed to a method of making a solid dosage bi-layer form of rosuvastatin and ezetimibe comprising the five steps enumerated below.

(a) Blending rosuvastatin calcium with pre-gelatinized starch, calcium hydrogen phosphate dihydrate, microcrystalline cellulose and crospovidone, passing through sieve and lubricating the blend with lubricant such as sodium stearyl fumarate to create the rosuvastatin layer blend. In the preferred embodiment of this step, rosuvastatin calcium is passed through a sieve, followed by pre-gelatinized starch, calcium hydrogen phosphate dihydrate, microcrystalline cellulose and crospovidone and blended, and then lubricated and blended with sodium stearyl fumarate and passed through another sieve.

(b) Mixing ezetimibe with a wetting agent such as sodium lauryl sulphate, and disperse material in sufficient quantity of Isopropyl alcohol and dichloromethane mixture. Also in the preferred embodiment, the material of ezetimibe mixed with sodium lauryl sulphate is slowly added to the mixture of isopropyl alcohol and dichloromethane. This step is important to avoid crystallization of ezetimibe, which may adversely affect dissolution of ezetimibe.

(c) Absorbing the dispersion on lactose or mannitol, and mix thoroughly. In the preferred embodiment of this step, the solution containing ezetimibe is added to the lactose or to the mannitol in a slow process to ensure ezetimibe solution is fully absorbed on lactose or mannitol, which results on full mounting of ezetimibe on lactose or mannitol without loss of assay.

(d) Air drying the dispersion, passing through sieve, and mix with croscarmellose sodium and blend. In the preferred embodiment of this step, the ezetimibe solution mounted on lactose or mannitol is dried evenly at temperatures between 30 degrees Celsius and 55 degrees Celsius. The temperature range avoids crystallization of ezetimibe that can adversely impact the dissolution of ezetimibe granules once process is fully complete. Additionally the ezetimibe mounted on lactose or mannitol should be air dried rather than oven dried to ensure an even flow of the ezetimibe mounting on lactose or mannitol.

(e) Mixing with polyvinylpyrrolidone solution and dry to obtain the ezetimibe granules. In the preferred embodiment the granules should be dried between 30 and 75 degrees Celsius.

(f) Creating the desired bi-layer tablet by compressing the two distinctly different set of granules as desired in the second aspect of the invention in a bi-layer compression machine, followed by film coating the oral dosage form.

Example 1: Fixed Combination Tablet of Rosuvastatin 20 mg and Ezetimibe 10 mg

Below is an example of the formulation of a bi-layer tablet with rosuvastatin 20 mg and ezetimibe 10 mg.

| Ingredients | Weight per tablet |
| --- | --- |
| Rosuvastatin | 22.08 |
| Pre-gelatinized starch and dicalcium phosphate | 16.8 |
| Microcrystalline cellulose | 140 |
| Crospovidone, Aerosil and butylated hydroxy anisole (BHA) | 42.1 |
| Total weight of the layer | 220.98 |

| Ingredients | Weight per tablet |
| --- | --- |
| Ezetimibe | 10.08 |
| Sodium lauryl sulphate and croscarmellose | 30 |
| Lactose | 80 |
| Polyvinylpyrrolidone and magnesium stearate | 2.92 |
| Total weight of the layer | 123 |

The method of the above formulation is undertaken in three stages as follows:

Stage A. Rosuvastatin granules: The steps followed to create the rosuvastatin granules are as follows:

1. Pass rosuvastatin through sieve, followed by pre-gelatinized starch, calcium hydrogen phosphate dihydrate, microcrystalline cellulose and crospovidone through the sieve.

2. Load the Step 1 material blend to Octagonal blender and blend.

3. Pass sodium stearyl fumarate through sieve, load in to Step 2 material and blend.

Stage B. Ezetimibe granules: The steps followed to create the ezetimibe granules are as follows:

1. Pass ezetimibe and sodium lauryl sulphate through sieve and mix.

2. Disperse Step-1 material in quantity sufficient of isopropyl alcohol and dichloromethane mixture.

3. The prepared Step-2 dispersion absorb on lactose, mix thoroughly and dried.

4. The Step-3 dried absorb pass through sieve and mix with previously passed croscarmellose sodium in octagonal blender or suitable container attached to octagonal blender.

5. The Step-4 mixed materials granulate with polyvinylpyrrolidone solution and dried.

6. The Step-5 dried granule pass through sieve and the passed granules lubricate with magnesium stearate in octagonal blender or suitable container attached to the blender.

Stage C. Combination of two layers

The rosuvastatin granules and ezetimibe bed layer granules compressed in bilayer compression machine. Compressed tablet is coated under continuous stirring.

Example 2: Fixed Combination Tablet of Rosuvastatin 10 mg and Ezetimibe 10 mg

Below is an example of the formulation of a bi-layer tablet with rosuvastatin 10 mg and ezetimibe 10 mg.

| Ingredients | Weight per tablet |
| --- | --- |
| Rosuvastatin | 11.04 |
| Pre-gelatinized starch and dicalcium phosphate | 8.4 |
| microcrystalline cellulose | 70 |
| Crospovidone, Aerosil and butylated hydroxyl anisole(BHA) | 21.05 |
| Total weight of the layer | 110.49 |

| Ingredients | Weight per tablet |
| --- | --- |
| Ezetimibe | 10.08 |
| Sodium lauryl sulphate and croscarmellose | 30 |
| Lactose | 80 |
| Polyvinylpyrrolidone and magnesium stearate | 2.92 |
| Total weight of the layer | 123 |

The method of the above formulation is undertaken in three stages as follows:

Stage A. Rosuvastatin granules: The steps followed to create the rosuvastatin granules are as follows:

1. Pass rosuvastatin through sieve, followed by pre-gelatinized starch, calcium hydrogen phosphate dihydrate, microcrystalline cellulose and crospovidone through the sieve.

2. Load the Step 1 material blend to Octagonal blender and blend.

3. Pass sodium stearyl fumarate through sieve, load in to Step 2 material and blend.

Stage B. Ezetimibe granules: The steps followed to create the ezetimibe granules are as follows:

1. Pass Ezetimibe and sodium lauryl sulphate through sieve and mix.

2. Disperse Step-1 material in quantity sufficient of isopropyl alcohol and dichloromethane mixture.

3. The prepared Step-2 dispersion absorb on lactose, mix thoroughly and dried.

4. The Step-3 dried absorb pass through sieve and mix with previously passed croscarmellose sodium in octagonal blender or suitable container attached to octagonal blender.

5. The Step-4 mixed materials granulate with polyvinylpyrrolidone solution.

6. The Step-5 dried granule pass through sieve and the passed granules lubricate with magnesium stearate in octagonal blender or suitable container attached to the blender.

Stage C. Combination of two layers

The rosuvastatin granules and ezetimibe bed layer granules compressed in bilayer compression machine. Compressed tablet is coated under continuous stirring.

Example 3

| Composition | mg |
| --- | --- |
| Rosuvastatin | 22.08 |
| Pre gelatinized starch and calcium hydrogen phosphate | 16.80 |
| Microcrystalline cellulose | 140 |
| Crospovidone, aerosol and butylated hydroxyl anisole | 42.1 |
| Total weight of Rosuvastatin layer (mg) | 220.98 |
| Ezetimibe | 10.98 |
| Sodium lauryl sulphate and croscarmellose | 30 |
| Mannitol | 80 |
| polyvinylpyrrollidone and magnesium stearate | 2.92 |
| Total weight of Ezetimibe layer (mg) | 123 |

The method of the above formulation is undertaken in three stages as follows:

Stage A. Rosuvastatin granules: The steps followed to create the rosuvastatin granules are as follows:

1. Pass rosuvastatin through sieve, followed by pre-gelatinized starch, calcium hydrogen phosphate dihydrate, microcrystalline cellulose and crospovidone through the sieve.

2. Load the Step 1 material blend to Octagonal blender and blend.

3. Pass sodium stearyl fumarate through sieve, load in to Step 2 material and blend.

Stage B. Ezetimibe granules: The steps followed to create the ezetimibe granules are as follows:

1. Pass Ezetimibe and sodium lauryl sulphate through sieve and mix.

2. Disperse Step-1 material in quantity sufficient of isopropyl alcohol and dichloromethane mixture.

3. The prepared Step-2 dispersion absorb on mannitol, mix thoroughly and dried.

4. The Step-3 dried adsorb pass through sieve and mix with previously passed croscarmellose sodium in octagonal blender or suitable container attached to octagonal blender.

5. The Step-4 mixed materials granulate with polyvinylpyrrolidone-solution.

6. The Step-5 dried granule pass through sieve and the passed granules lubricate with magnesium stearate in octagonal blender or suitable container attached to the blender.

Stage C. Combination of two layers

The rosuvastatin granules and ezetimibe bed layer granules compressed in bilayer compression machine. Compressed tablet is coated under continuous stirring.

Dissolution Results

Dissolution is a well-established method to test pharmaco-equivalence of two products. The pharmaco-equivalence of the fixed-combination dosage forms of the present invention was compared with that of the corresponding free-combinations. Table 2 and Table 3 list the results from the Example 2 described earlier and of multiple tests that were undertaken between the test (fixed-combination) and the reference (free-combination) dosage forms. The results of tablets according to Example 3 are similar.

TABLE 2

COMPARATIVE DISSOLUTION PROFILE OF CRESTOR 20 MG AND ROSUVASTATIN CALCIUM FROM ROSUVASTATIN 20 mg & EZETIMIBE 10 mg TABLETS

| Time in min | Crestor - 20 mg tablets (B.No: HV373) REFERENCE | Rosuvastatin from the test tablets of Inventor TEST | Within acceptable range to be comparable |
|---|---|---|---|
| 10 | 96 | 84 | YES |
| 20 | 97 | 93 | |
| 30 | 97 | 95 | |
| 45 | 97 | 98 | |

TABLE 3

COMPARATIVE DISSOLUTION PROFILE OF EZETROL 10 MG AND EZETIMIBE FROM ROSUVASTATIN 20 mg & EZETIMIBE 10 mg TABLETS

| Time in min | Ezetrol 10 mg tablets (B.No: 310688) REFERENCE | Ezetimibe from the test tablets of Inventor TEST | Within acceptable range to be comparable |
|---|---|---|---|
| 10 | 95 | 78 | YES |
| 20 | 95 | 83 | |
| 30 | 95 | 90 | |
| 45 | 95 | 95 | |

Stability Results

To test the stability of the formulation, inventors undertook stability test of the formulation. Following are the results of accelerated stability studies of formulations. The tablets of examples 1, 2 and 3 were exposed to accelerated stability conditions such as 40° C./75% relative humidity (RH) in unsealed high-density polyethylene (HDPE) containers (open condition) for the period of two months. Samples were analyzed each week for degradation products and assay. Summary results are enumerated below in Table 4.

TABLE 4

RELATED SUBSTANCE IMPURITIES FOR ROSUVASTATIN AND EZETIMIBE

| Impurity Name | limit | 3 weeks 40° C./75% RH | 6 weeks 40° C./75% RH |
|---|---|---|---|
| Rosuvastatin related lactone | Not more than 0.5% | 0.006% | 0.16% |
| Rosuvastatin related keto-impurity | Not more than 0.5% | 0.15% | 0.15% |
| Ezetimibe related cyclic ether impurity | Not more than 0.5% | Not detected | Not detected |

The results of above accelerated stability studies depict stabilization potential of the formulation as well as the improved absorption and dissolution of ezetimibe with the novel process.

In a fourth embodiment, this invention is directed to solid dosage forms of rosuvastatin and ezetimibe made according to the method of the third embodiment.

Fifth embodiment of this invention is directed to a method of treating hyperlipidemia, cardiovascular diseases, congestive heart failure, myocardial infarction, atherosclerosis comprising administering a solid dosage form of rosuvastatin and ezetimibe in combination to a patient in need of such a treatment. In a preferred embodiment, the solid dosage form is orally administered to the subject.

While this invention has been particularly shown and described with references to preferred embodiments thereof, it will be understood by those skilled in the art that various changes in form and details may be made therein without departing from the scope of the invention encompassed by the appended claims.

What is claimed is:

1. A solid dosage form of rosuvastatin and ezetimibe combined in one bilayer tablet comprising rosuvastatin in a first layer and ezetimibe in a second layer in a weight ratio of 0.5:1, 1:1 or 2:1, and wherein:
   (i) rosuvastatin is formulated with microcrystalline cellulose in the first layer and ezetimibe is formulated without microcrystalline cellulose in the second layer;
   (ii) the first layer comprises rosuvastatin and 1-15 wt % of pharmaceutically acceptable excipients; 0.5-10 wt % of dicalcium phosphate; 20-90 wt % of microcrystalline cellulose; 2-30 wt % of crospovidone; and 0.1-2 wt % of pharmaceutically acceptable lubricants; wherein all weight percents are based on the total weight of the first layer;
   (iii) the second layer comprises ezetimibe and 2-20 wt % of pharmaceutically acceptable excipients; 20-90 wt % of mannitol; 0.5-10 wt % of binders; and 0.2-5 wt % of magnesium stearate; wherein all weight percents are based on the total weight of the second layer;
   (iv) said solid dosage releases 98% of rosuvastatin and 95% of ezetimibe within 45 minutes as measured by a standard in vitro dissolution test; and wherein about 50% of the maximum concentration of rosuvastatin and about 100% of the maximum concentration of ezetimibe are absorbed in vivo into the circulation of healthy humans within 1 hour after administering; and
   (v) said solid dosage form is a stable composition of rosuvastatin and ezetimibe comprising less than 0.5% of ezetimibe related impurities after 6 weeks of storage at 40° C. and 75% relative humidity, less than 0.5% of rosuvastatin related lactone impurities and less than 0.5% of rosuvastatin related keto impurities after 6 weeks of storage at 40° C. and 75% relative humidity.

2. The solid dosage form of claim 1, wherein the rosuvastatin dosage ranges from 2.5 mg to 40 mg, and ezetimibe dosage ranges from 5 mg to 20 mg.

3. The solid dosage form of claim 1, comprising no ezetimibe related impurities after 6 weeks at 40° C. and 75% relative humidity, less than 0.2% of rosuvastatin related lactone impurities and less than 0.2% of rosuvastatin related keto impurities after 6 weeks of storage at 40° C. and 75% relative humidity.

4. The solid dosage form of claim 1, wherein the first layer additionally contains 0.05-2 wt % of butylated hydroxyanisole as an antioxidant and 1-10 wt % of fumed silica as a dispersion agent; and wherein all weight percents are based on the total weight of the first layer.

5. A method of making a solid oral dosage form of claim 1, the method comprising the steps of:

a) blending rosuvastatin calcium with pre-gelatinized starch, calcium hydrogen phosphate dihydrate, microcrystalline cellulose and crospovidone to provide a blend, and passing the blend through a sieve and lubricating the blend with a lubricant to create a rosuvastatin layer blend;

b) mixing ezetimibe with a wetting agent and a disperse material in isopropyl alcohol and dichlormethane mixture;

c) absorbing the dispersion of step b) on mannitol, and mixing thoroughly;

d) air drying the dispersion of step c) passing through the sieve, mixing with croscarmellose sodium, and blending;

e) granulating the mix of step d) with a polyvinylpyrrolidone solution and drying to obtain the ezetimibe granules; and f) creating a bilayer tablet by compressing the blend of step a) and the granules of step e) in a bilayer compression machine, followed by film coating.

6. A method of treating hyperlipidemia, cardiovascular diseases, congestive heart failure, myocardial infarction, or atherosclerosis, said method comprising administering orally the solid dosage form of claim 1 to a patient in need of such treatment.

7. The method of claim 5, wherein the lubricant in step a) is sodium stearyl fumarate and the wetting agent in step b) is sodium lauryl sulfate.

* * * * *